(12) United States Patent
Kivioja et al.

(10) Patent No.: US 11,730,558 B2
(45) Date of Patent: Aug. 22, 2023

(54) COLOR CODING

(71) Applicant: Picosun Oy, Espoo (FI)

(72) Inventors: Jani Kivioja, Masala (FI); Niku Oksala, Masala (FI)

(73) Assignee: Picosun Oy, Espoo (FI)

( * ) Notice: Subject to any disclaimer, the term of this patent is extended or adjusted under 35 U.S.C. 154(b) by 461 days.

(21) Appl. No.: 16/832,203

(22) Filed: Mar. 27, 2020

(65) Prior Publication Data

US 2020/0305998 A1 Oct. 1, 2020

Related U.S. Application Data

(60) Provisional application No. 62/826,048, filed on Mar. 29, 2019.

(51) Int. Cl.
*A61B 90/00* (2016.01)
*A61L 29/08* (2006.01)
*A61B 90/92* (2016.01)
*C23C 16/455* (2006.01)
*A61L 31/14* (2006.01)
*A61B 17/00* (2006.01)
*A61L 31/08* (2006.01)
*A61B 17/072* (2006.01)
*A61L 29/14* (2006.01)

(52) U.S. Cl.
CPC ............ *A61B 90/08* (2016.02); *A61B 90/92* (2016.02); *A61L 29/08* (2013.01); *A61L 31/14* (2013.01); *C23C 16/45555* (2013.01); *A61B 17/072* (2013.01); *A61B 2017/00526* (2013.01); *A61B 2090/0803* (2016.02); *A61B 2090/0807* (2016.02); *A61L 29/14* (2013.01); *A61L 31/08* (2013.01)

(58) Field of Classification Search
CPC ............ A61B 1/00142; A61B 17/072; A61B 17/07292; A61B 18/14; A61B 18/1442; A61B 18/1445; A61B 46/10; A61B 46/13; A61B 90/92; A61B 90/08; A61B 90/0803; A61L 29/08; A61L 29/14; A61L 31/08; A61L 31/14
USPC ....... 227/19, 175.1; 606/45, 51, 139, 219, 1; 424/78.35, 78.37, 400
See application file for complete search history.

(56) References Cited

U.S. PATENT DOCUMENTS

| | | |
|---|---|---|
| 4,981,756 A | 1/1991 | Rhandhawa |
| 5,518,927 A | 5/1996 | Malchesky et al. |
| 5,573,529 A | 11/1996 | Haak et al. |
| 7,427,394 B2 * | 9/2008 | Anderson ............ C12N 15/88 424/78.37 |
| 8,211,235 B2 | 7/2012 | Lindfors et al. |

(Continued)

FOREIGN PATENT DOCUMENTS

| | | |
|---|---|---|
| EP | 0914833 A2 | 5/1999 |
| WO | 2014145492 A2 | 9/2014 |
| WO | 2015107476 A1 | 7/2015 |

OTHER PUBLICATIONS

European Patent Office, Extended European Search Report, Application No. 20165505.7-1101, dated Aug. 20, 2020, 8 Pages.

*Primary Examiner* — Scott A Smith
(74) *Attorney, Agent, or Firm* — Ziegler IP Law Group, LLC

(57) ABSTRACT

A medical instrument, including an atomic layer deposition, ALD, coating to indicate the type of the medical instrument, and use of ALD to indicate number of re-uses of a medical instrument.

9 Claims, 3 Drawing Sheets

(56) References Cited

U.S. PATENT DOCUMENTS

| | | | |
|---|---|---|---|
| 8,303,582 B2* | 11/2012 | Cunningham | A61B 18/14 |
| | | | 606/51 |
| 8,394,095 B2* | 3/2013 | Garrison | A61B 18/1445 |
| | | | 606/45 |
| 9,327,416 B2 | 5/2016 | Madeira et al. | |
| 9,968,715 B2 | 5/2018 | Keil et al. | |
| 2003/0083646 A1* | 5/2003 | Sirhan | A61F 2/91 |
| | | | 623/1.42 |
| 2003/0220637 A1* | 11/2003 | Truckai | A61B 18/1442 |
| | | | 606/51 |
| 2007/0020469 A1* | 1/2007 | Wood | B82Y 30/00 |
| | | | 428/411.1 |
| 2007/0054412 A1* | 3/2007 | Cregger | C09B 21/00 |
| | | | 436/166 |
| 2009/0175819 A1* | 7/2009 | Priest | A61P 37/00 |
| | | | 435/7.1 |
| 2010/0069904 A1 | 3/2010 | Cunningham | |
| 2010/0086678 A1* | 4/2010 | Arthur | C09J 171/02 |
| | | | 528/392 |
| 2010/0298754 A1* | 11/2010 | Ostfeld | A61M 5/00 |
| | | | 607/9 |
| 2012/0066956 A1 | 3/2012 | Lyngstadaas et al. | |
| 2014/0127270 A1* | 5/2014 | Amarnani | A61B 1/00142 |
| | | | 424/78.37 |
| 2014/0154808 A1 | 6/2014 | Patel | |
| 2016/0060758 A1 | 3/2016 | Marquardt et al. | |
| 2016/0186307 A1 | 6/2016 | Sukadhare et al. | |
| 2016/0250389 A1 | 9/2016 | Keil et al. | |
| 2019/0093150 A1* | 3/2019 | Laible | A01N 25/34 |
| 2020/0305998 A1* | 10/2020 | Kivioja | A61B 90/92 |

* cited by examiner

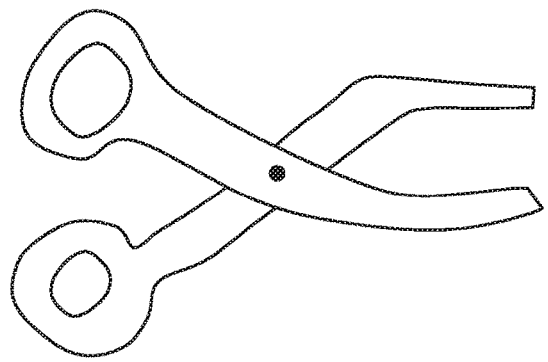
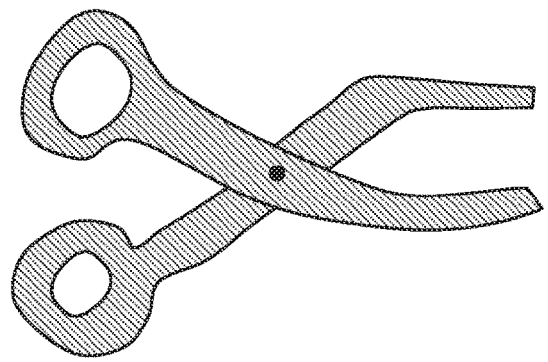
Fig. 1a Fig. 1b
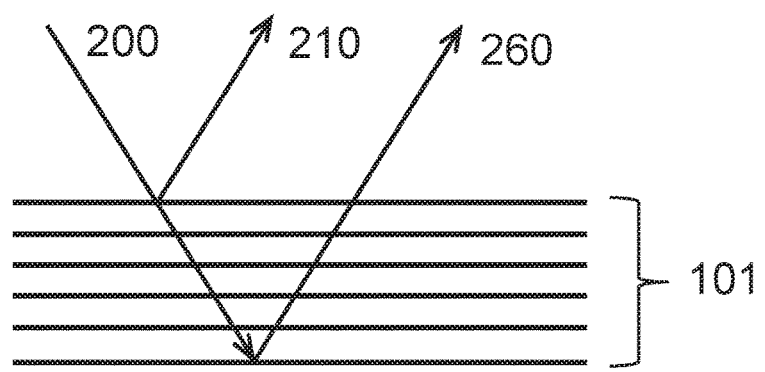
Fig. 2

COLOR CODING

FIELD

The disclosed embodiments generally relate to coatings and their manufacturing methods.

BACKGROUND

This section illustrates useful background information without admission of any technique described herein representative of the state of the art.

Currently, instruments used in surgical operations (for example forceps, scissors, needle holders, retractors, endoscopes, knife shafts but not limited to these) are marked using marker tapes or engravings to indicate whether the instrument is disposable (i.e. single-use instrument) or can be used for several times (i.e. reusable). Some instruments are complex in shape, do not withstand the process of sterilization or reprocessing, i.e. the device characteristics may be altered resulting in impaired performance, failure, absorb unwanted chemicals or toxins, corrode, are not tested for multiple use, may cause cross-infection, and are therefore made disposable. Surgical instruments become soiled and contaminated by micro-organisms when used on patients and must therefore undergo sterilization to clean and disinfect them thoroughly. If the process is inadequate, biological debris or chemical compounds used in the process accumulate in the instruments and this may predispose the patient to infection or tissue irritation. Instruments validated to be used for several times tolerate sterilization, have low risk of accumulating biological debris or chemicals used in the process and have low risk of technical malfunction. Exposure of a single-use disposable instrument to sterilization and multiple uses poses a potential hazard in the form of malfunction, accumulation of chemicals or infection.

SUMMARY

It is an object of certain embodiments to facilitate the identification of different types of medical instruments.

It is an object of certain further embodiments to assist in evaluating the general condition of a reusable medical instrument.

According to a first example aspect of the disclosed embodiments there is provided a medical instrument as defined the appended patent claim 1.

Embodiments of the first aspect are defined in dependent patent claims.

According to a second example aspect of the disclosed embodiments there is provided a method as defined in appended patent claim 8.

According to a third example aspect of the disclosed embodiments there is provided a use of an ALD coating on a surface of a medical instrument as defined in appended patent claim 9.

According to an example aspect of the disclosed embodiments there is provided a medical instrument, comprising:

an atomic layer deposition, ALD, coating to indicate the type of the medical instrument.

According to another example aspect there is provided use of ALD to indicate a type of a medical instrument.

In certain embodiments, there are provided two types of medical instruments: disposable medical instruments and reusable medical instruments.

In certain embodiments, there is provided a codebook defining pre-defined coating parameter(s) matching the type of the medical instrument. In certain embodiments, the coating parameter(s) include layer thickness. In certain embodiments, the coating parameter(s) include layer material.

According to another aspect of the disclosed embodiments there is provided a medical instrument comprising:

a plurality of ALD layers configured to be peeled off one-by-one (i.e., separately, one after the other) by a pre-determined process to indicate the number of re-uses performed with the medical instrument.

In certain embodiments, the pre-determined process is a sterilization process.

According to another example aspect there is provided a method of depositing a coating onto a medical instrument, comprising:

providing pre-defined coating parameter(s) matching the type of the medical instrument; and depositing a coating by ALD onto the medical instrument based on said coating parameter(s).

According to another example aspect there is provided a medical instrument comprising:

a coating on a surface of the medical instrument, wherein the coating comprises a plurality of ALD layers, the coating indicating the number of re-uses experienced by the medical instrument.

In certain aspects or embodiments, a medical instrument concerned is marked by ALD (so that its type becomes clear). In certain aspects or embodiments, the wearing of a medical instrument or the condition of the medical instrument is monitored by following the color of an ALD coating deposited on the surface of the medical instrument.

In certain aspects of embodiments, enhanced properties of the medical instrument are provided. Examples of enhanced properties are preventing it from absorbing chemicals, biological debris, bacteria, toxins, preventing corrosion, preventing magnetization, and improving durability in the long term.

In certain embodiments, the same ALD coating material (e.g., $HfO_2$,) with different thicknesses is used to code the usage purpose of the item (medical instrument) to minimize errors.

In certain embodiments, for re-usable items, each sterilization step (e.g., an autoclave processing) removes one well defined outer layer of a coating. The color of the coating/item tells how many times the item is re-used.

In certain embodiments, the thickness of the coating (in total) is less than 200 nm. In certain embodiments, the coating is implemented as a laminate structure. In certain embodiments, the base material of the medical instrument is metal. In certain embodiments, the coating material is a metal oxide.

In certain embodiments, the coating is a MLD coating. More generally, the said coating on a surface of the medical instrument comprises a plurality of layers, not necessarily ALD layers, but layers deposited based on a selected vapor-deposition based technique.

Different non-binding example aspects and embodiments have been presented in the foregoing. The above embodiments and embodiments described later in this description are used to explain selected aspects or steps that may be utilized in implementations of the disclosed embodiments. It should be appreciated that corresponding embodiments apply to other example aspects as well. Any appropriate combinations of the embodiments can be formed.

BRIEF DESCRIPTION OF THE DRAWINGS

The disclosed embodiments will now be described, by way of example only, with reference to the accompanying drawings, in which:

FIGS. 1a and 1b show marking the type of medical instruments in accordance with certain embodiments;

FIG. 2 shows how the thickness of a coating on a medical instrument defines the color of the coating in accordance with certain embodiments;

DETAILED DESCRIPTION

Figure 3:
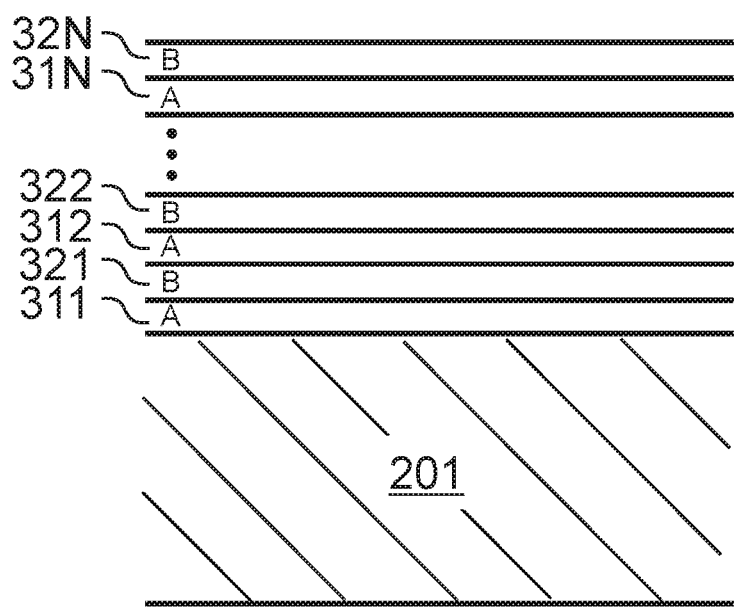
FIG. 3 shows a nanolaminate structure in accordance with certain embodiments.

In the following description, Atomic Layer Deposition (ALD) technology is used as an example.

The basics of an ALD growth mechanism are known to a skilled person. ALD is a special chemical deposition method based on the sequential introduction of at least two reactive precursor species to at least one substrate. It is to be understood, however, that one of these reactive precursors can be substituted by energy when using, for example, photon-enhanced ALD or plasma-assisted ALD, for example PEALD, leading to single precursor ALD processes. For example, deposition of a pure element, such as metal, requires only one precursor. Binary compounds, such as oxides can be created with one precursor chemical when the precursor chemical contains both of the elements of the binary material to be deposited. Thin films grown by ALD are dense, pinhole free and have uniform thickness.

The at least one substrate is typically exposed to temporally separated precursor pulses in a reaction vessel to deposit material on the substrate surfaces by sequential self-saturating surface reactions. In the context of this application, the term ALD comprises all applicable ALD based techniques and any equivalent or closely related technologies, such as, for example the following ALD sub-types: MLD (Molecular Layer Deposition), plasma-assisted ALD, for example PEALD (Plasma Enhanced Atomic Layer Deposition) and photon-enhanced Atomic Layer Deposition (known also as photo-ALD or flash enhanced ALD).

A basic ALD deposition cycle consists of four sequential steps: pulse A, purge A, pulse B and purge B. Pulse A consists of a first precursor vapor and pulse B of another precursor vapor. Inactive gas and a vacuum pump are typically used for purging gaseous reaction by-products and the residual reactant molecules from the reaction space during purge A and purge B. A deposition sequence comprises at least one deposition cycle. Deposition cycles are repeated until the deposition sequence has produced a thin film or coating of desired thickness. Deposition cycles can also be either simpler or more complex. For example, the cycles can include three or more reactant vapor pulses separated by purging steps, or certain purge steps can be omitted. On the other hand, photo-enhanced ALD has a variety of options, such as only one active precursor, with various options for purging. All these deposition cycles form a timed deposition sequence that is controlled by a logic unit or a microprocessor.

When different materials are used as different thin film layers on top of each other, they are referred to as laminates or nanolaminate.

The deposition device, comprising means of altering the required materials to be deposited (or the laminate structure), is a reactor apparatus preferably configured to exploit principles of a selected vapor-deposition based technique. In terms of an overall implementation, the reactor may be based on an ALD installation described in the U.S. Pat. No. 8,211,235 (Lindfors), for example, or on the installation "Picosun R-200 Advanced ALD system" available from Picosun Oy, Finland. Nevertheless, the features underlying a concept of the disclosed embodiments can be incorporated into any other chemical deposition reactor embodied as an ALD, PEALD (Plasma-Enhanced ALD), MLD (Molecular Layer Deposition) or CVD (Chemical Vapor Deposition) device, for example.

FIGS. 1a and 1b show marking the type of medical instruments in accordance with certain embodiments. FIG. 1a shows a single use instrument. In certain embodiments, the single use instrument is processed by ALD to deposit a coating that appears in a first color, or the single use instrument may be left uncoated. FIG. 1b shows a reusable instrument. In certain embodiments, the reusable instrument is processed by ALD to deposit a coating that appears in a second color that is different from the first color to differentiate from the single use instrument.

FIG. 2 shows how the thickness of a coating on a medical instrument (such as surgical or dental instrument) defines the color of the coating in accordance with certain embodiments. An ALD coating 101 with a thickness is deposited onto a base material 201, which may be stainless steel for example. Incident light 200 reflects 210 from the surface of the coating 101. A ray of light that propagates into inside of the coating 101 reflects 260 from the interface between the base material 201 and the coating 101. An interference of the reflected rays 210 and 260 causes the reflected light to appear in a color different from the color of the incident light. Since the thickness of the coating is a multiple of atomic layers, a difference in interference is a function of the atomic layer thickness and therefore predictable. A certain coating thickness appears in a predictable color. The thickness of the coating is therefore derivable from the color appearance. Further, different materials deposited with ALD give different predictable effects of color appearance with respect to thickness. For example, removal of a certain thickness of a first material causes different predictable changes in color appearance compared to removal of the same thickness of another material. In certain embodiments, the refractive index of the structure is varied based on material selection, which will affect the external appearance of the coated surface in a predictive manner.

The horizontal lines within the coating 101 in FIG. 2 illustrate that the layer thickness of the coating may be originally different, or the thickness may become reduced as the coating wears off (or due to removal of atomic layers, or conformal ALD monolayers one-by-one, in sterilization processes for example).

Depending on the coating material and its thickness the color of the coating/medical instrument or differences in the color can be seen by bare eyes or by a scanner. In certain embodiments, it is immediately visible from a set of medical instruments waiting for sterilization which of them are disposable instruments and which are reusable.

FIG. 3 shows a nanolaminate structure deposited on the base material 201. The nanolaminate structure comprises material layers or coatings of different coating materials A and B on top of each other in an alternating fashion.

Figure 4:
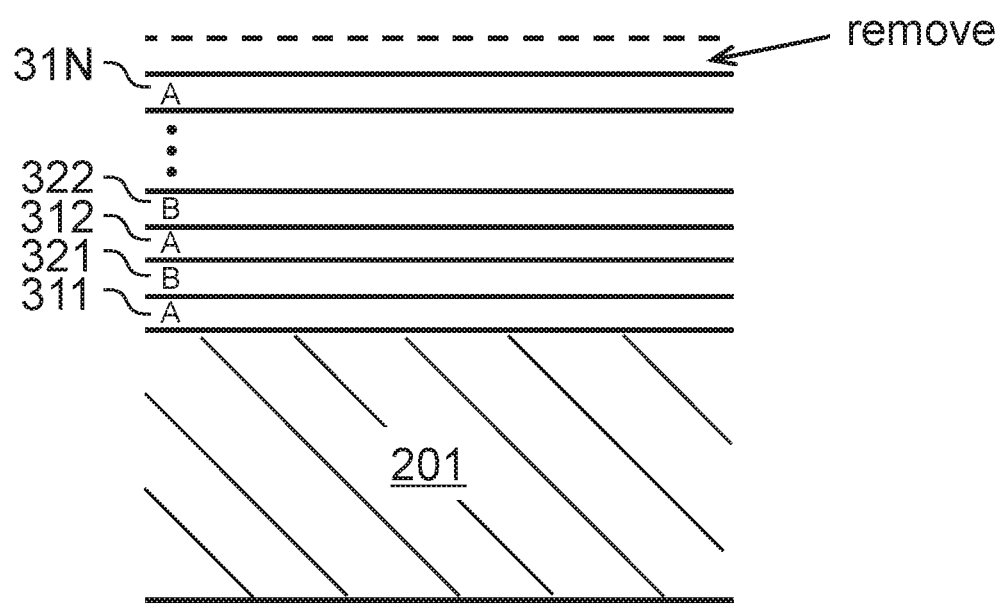
FIG. 4 shows using the structure of FIG. 3 in predicting the number of re-uses in accordance with certain embodiments.

FIG. 4 shows using the structure of FIG. 3 in predicting the number of re-uses in accordance with certain embodiments. In each sterilization step (e.g., exposing the medical instrument to sterilizing liquid or steam) a layer of the nanolaminate structure dissolves, and a corresponding change in the color of the coating occurs. The number of re-uses of the medical instrument is derived from the color of the coating/medical instrument.

Figure 5:
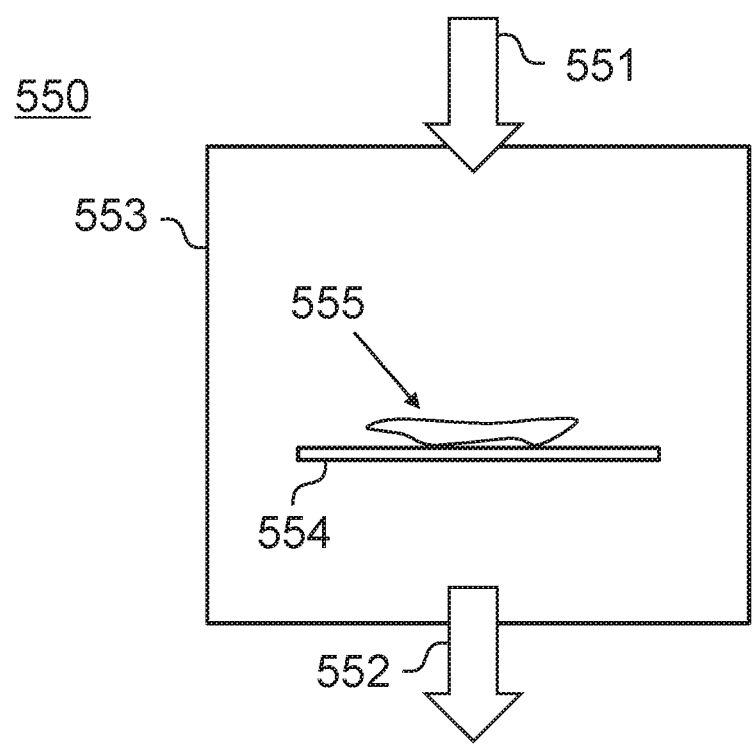
FIG. 5 shows a substrate processing apparatus in accordance with certain embodiments.

FIG. 5 shows a substrate processing apparatus (or deposition reactor) 550 in accordance with certain embodiments. The apparatus 550 comprises a reaction chamber 553, and at least one coating material inlet 551 to the reaction chamber 553. The apparatus 550 further comprises a fore-line 552 to a pump (for exhaust of gases). In the embodiment shown in FIG. 5, the inlet 551 for the coating material (or reactive chemical) is positioned in a top section of the reaction chamber 553 and the fore-line 552 in a bottom section, the general flow direction within the reaction chamber 553 thus being vertical (downwards).

A substrate support 554 supports a medical instrument 555 loaded into the reaction chamber 553 for example from a side. The medical instrument 555 is processed by ALD to produce a coating with a pre-determined number of layers of pre-determined material(s).

Without limiting the scope and interpretation of the patent claims, certain technical effects of one or more of the example embodiments disclosed herein are listed in the following. A technical effect is facilitating the identification of different types of medical instruments. Another technical effect is providing color coding of medical instruments by ALD. Another technical effect is aiding in predicting the number of re-uses of medical instruments.

The foregoing description has provided by way of non-limiting examples of particular implementations and embodiments a full and informative description of the best mode presently contemplated by the inventors for carrying out the disclosed embodiments. It is however clear to a person skilled in the art that the disclosed embodiments are not restricted to details of the embodiments presented above, but that it can be implemented in other embodiments using equivalent means without deviating from the characteristics of the disclosed embodiments.

Furthermore, some of the features of the above-disclosed embodiments may be used to advantage without the corresponding use of other features. As such, the foregoing description should be considered as merely illustrative of the principles of the disclosed embodiment, and not in limitation thereof. Hence, the scope of the disclosed embodiments are only restricted by the appended patent claims.

The invention claimed is:

1. A medical instrument, comprising:
a coating on a surface of the medical instrument comprising a plurality of ALD layers configured to be removed separately, one-by-one, one after the other, by a pre-determined process, where a number of removed layers indicate a number of re-uses performed with the medical instrument.

2. The medical instrument of claim 1, wherein the coating indicates the number of re-uses experienced by the medical instrument.

3. The medical instrument of claim 1, wherein the coating indicates the number of re-uses by a color appearance of the coating.

4. The medical instrument of claim 3, comprising said coating to indicate the number of re-uses seen by bare eyes or by a scanner.

5. The medical instrument of claim 1, wherein the pre-determined process is a sterilization process or an autoclave process.

6. The medical instrument of claim 1, comprising metal as a base material on which said plurality of ALD layers is deposited.

7. The medical instrument of claim 1, wherein the coating comprises a nanolaminate structure deposited on a base material, the nanolaminate structure comprising alternating first and second material layers, wherein the first and second material layers are of different material.

8. A method, comprising:
loading a medical instrument into a reaction chamber of a deposition reactor;
depositing, by ALD, a coating on a surface of the medical instrument comprising a plurality of conformal ALD monolayers configured to be removed separately, one-by-one, one after the other, by a pre-determined process to, where a number of removed conformal ALD monolayers indicate a number of re-uses performed with the medical instrument.

9. Use of an ALD coating on a surface of a medical instrument, where a number of removed layers of the ALD coating indicate a number of re-uses of the medical instrument.

* * * * *